May 8, 1956
R. REGAN
Plant Pat. 1,477
LANTANA PLANT
Filed June 7, 1955
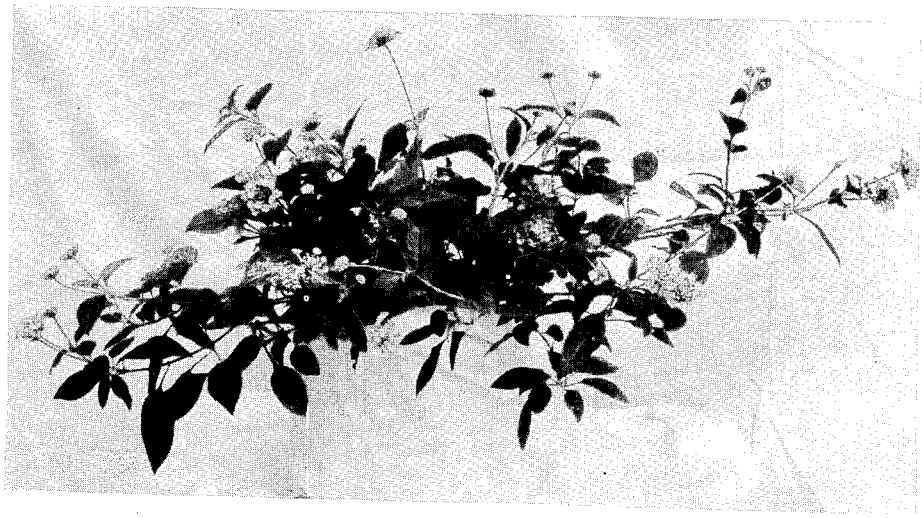
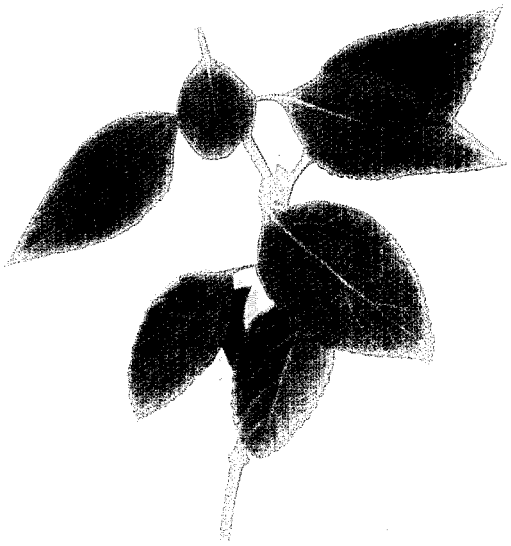
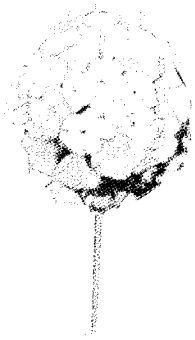
INVENTOR.
RONALD REGAN
BY J. F. Cuneo
ATTORNEY United States Patent Office Plant Pat. 1,477
Patented May 8, 1956

1,477

LANTANA PLANT

Ronald Regan, Monterey Park, Calif., assignor to Monrovia Nursery Co., Monrovia, Calif., a corporation of California Application June 7, 1955, Serial No. 513,923

1 Claim. (Cl. 47—60)

The present invention relates to a new and distinct variety of the lantana genus, which has resulted from cross breeding by me of *Lantana callowiana* Goldrush, United States Plant Patent No. 1211 and *Lantana camara* Radiation, an unpatented variety, after conducting a considerable number of experiments in Southern California, particularly Los Angeles County. Cross breeding the above named species of lantana has produced a new type as well as a new variety of lantana that combines some of the characteristics of each of the parent plants. The new variety of lantana differs in particular from its parent plant, *Lantana callowiana* Goldrush, in that its flowers are orange-red in color with some of the centrally positioned florets sometime shading to an apricot tint, and the leaves are much larger and of a deeper shade of green. This plant is a vigorous grower. My novel plant differs from the other parent plant, *Lantana camara* Radiation in that its growth is prostrate and the plant has many branches. The bloom of the novel plant is made up of a number of florets in an umbel with the number of florets varying in each umbel.

The accompanying illustrations include a black and white photograph of the new orange-red variety that clearly shows its prostrate or trailing habit. The illustration also includes a full color reproduction of a single umbel as well as that of a leaf branch.

The new variety of lantana has been reproduced asexually by me in Southern California by means of cuttings, and it has been noted that the distinguishing characteristics of the resulting plants appear to be well established. This new variety cannot be reproduced by sexual means since the plant will not reproduce true from seed.

The following is a detailed description of the novel variety. All color names and numbers which are used in the description of the plant and flowers are based on the Horticultural Colour Guide adopted by the British Colour Council.

THE PLANT

*Nature and growth*

The plant is best described as trailing and has many branches as shown in the accompanying photograph. The plant forms a prostrate, densely foliated shrub with vinelike stems up to three inches in length. The growth emanates from a central root.

*Stems*

The stems are slender and vinelike and are best described as woody.

*Leaves*

The foliage is persistent and ranges between moderately dense to very dense.

*Size.*—The leaves will average about one and one-half inches in width and about two and one-half inches in length.

*Shape.*—The leaves are described as broadly ovate, having serrated edges, with an apex that is acute-aristate; the base being rounded.

*Arrangement.*—The leaves are opposite, the pairs alternating approximately 90° at about every two inches. The leaves are attached to the stem by a short peduncle.

*Color.*—Parsley Green 00962.

*Appearance and texture.*—The surfaces of the leaves are sparsely pubescent, being slightly creased and having a leathery appearance. The ribs are quite prominent.

*Aroma.*—The leaves have a faint odor resembling somewhat the aroma of oil of eucalyptus.

*Blooming habit*

The plant is a profuse bloomer.

THE FLOWER

*Arrangement*

The flowers form in substantially hemispherical umbels which may vary between one inch and one and one-half inches in diameter. Each umbel may contain from ten to thirty individual florets, the average number of florets being between twenty and twenty-five. The umbels are produced on strong axillary peduncles, sometimes as long as three inches. The peduncles are slightly pubescent and the flowers form almost entirely on terminal growth.

*Florets*

The individual florets in the clusters are quite small.

*Color.*—Signal Red No. 719 for the majority of the florets, but sometimes the center of the umbel will have a few florets that are Apricot No. 609.

*Corolla.*—Usually irregular consisting of two petals and two lobes.

*Aroma.*—The flowers have a faint aroma which is similar to that of the leaves, resembling somewhat the odor of oil of eucalyptus.

Having described my invention, I claim:

The new and distinct variety of lantana plant, substantially as herein shown and described, characterized especially by its abundance of faintly aromatic flowers and its combination of the prostrate, trailing growth habit of *Lantana callowiana* Goldrush, with the orange-red flower coloration of *Lantana camara* Radiation.

No references cited.